United States Patent

Matsuoka et al.

[11] Patent Number: 5,891,029
[45] Date of Patent: Apr. 6, 1999

[54] METHOD OF AND DEVICE FOR POSITIONING A LIVING BODY FOR BIOLOGICAL MEASUREMENT AND APPARATUS FOR MEASUREMENT OF BIOLOGICAL INFORMATION

[75] Inventors: Koji Matsuoka; Yoshio Mitsumura; Harumi Uenoyama; Kexin Xu, all of Kyoto, Japan

[73] Assignees: Kyoto Daiichi Kagaku Co., Ltd., Kyoto; Kurashiki Boseki Kabushiki Kaisha, Okayama-ken, both of Japan

[21] Appl. No.: 776,775

[22] PCT Filed: Jun. 7, 1996

[86] PCT No.: PCT/JP96/01551

§ 371 Date: Feb. 7, 1997

§ 102(e) Date: Feb. 7, 1997

[87] PCT Pub. No.: WO96/41568

PCT Pub. Date: Dec. 27, 1996

[30] Foreign Application Priority Data

Jun. 9, 1995 [JP] Japan .................................. 7-143276

[51] Int. Cl.⁶ ................................................ A61B 5/00
[52] U.S. Cl. ..................... 600/407; 600/310; 356/244; 356/247; 356/39; 356/372
[58] Field of Search ..................... 128/633, 639, 128/653.1, 630, 632, 664, 897, 898; 607/79, 88; 356/39, 40, 256; 600/310, 372, 407, 300, 309, 473

[56] References Cited

U.S. PATENT DOCUMENTS

| | | |
|---|---|---|
| 3,696,456 | 10/1972 | Dunham et al. . |
| 4,195,641 | 4/1980 | Joines et al. ............................ 128/632 |
| 4,809,698 | 3/1989 | Kogo ...................................... 128/632 |
| 4,817,610 | 4/1989 | Lee ........................................ 128/630 |
| 4,926,866 | 5/1990 | Lee ........................................ 128/630 |
| 4,976,705 | 12/1990 | Aki et al. ................................ 604/304 |
| 5,038,492 | 8/1991 | Saaski et al. ........................ 422/82.09 |
| 5,237,994 | 8/1993 | Goldberger ............................ 128/633 |
| 5,299,572 | 4/1994 | Chen et al. ............................. 128/639 |
| 5,307,813 | 5/1994 | Young ................................. 128/653.4 |
| 5,638,818 | 6/1997 | Diab et al. ........................... 128/653.1 |
| 5,655,530 | 8/1997 | Messerschmidt ...................... 128/633 |

FOREIGN PATENT DOCUMENTS

| | | |
|---|---|---|
| 2821247A1 | 11/1979 | Germany . |
| 4224827A1 | 1/1994 | Germany . |
| WO87/00028A1 | 1/1987 | WIPO . |

*Primary Examiner*—Marvin M. Lateef
*Assistant Examiner*—Shawna J. Shaw
*Attorney, Agent, or Firm*—Birch, Stewart, Kolasch & Birch, LLP

[57] ABSTRACT

To secure a highly accurate measurement value of biological information with minimized variation by positioning a target part of a living body with good reproducibility and by positioning the target part of the living body easily with high reproducibility without pressing blood vessels in the living body. The concentration of a particular component in the living body is measured by the use of a transmitted or reflected spectrum obtained by projecting light onto the target part of the living body. A biological information measuring template 2 includes a shape memory medium 6 having a contact surface which, when the target part is pressed to the contact surface, undergoes change according to the shape of the target part, to thereby store the shape. The target part 1 of the living body is arranged at a store portion of the shape memory medium and is illuminated by light. The spectrum of light transmitted through or reflected from the target part 1 is arithmetically processed in an arithmetic control means 4 to calculate the concentration of the particular component in the living body, a result of calculation being outputted to an output unit 5.

8 Claims, 11 Drawing Sheets

METHOD OF AND DEVICE FOR POSITIONING A LIVING BODY FOR BIOLOGICAL MEASUREMENT AND APPARATUS FOR MEASUREMENT OF BIOLOGICAL INFORMATION

FIELD OF TECHNOLOGY

The present invention relates to a living body positioning method for positioning a target part of a living body during noninvasive measurement of the concentration of a particular component in the living body by the use of a transmitted or reflected spectrum that is obtained by illuminating the target part of the living body, a positioning device for the biological information measurement, and a biological information measuring apparatus.

BACKGROUND ART

In carrying out this kind of measurement, in order to attain consistent conditions for measurement of the spectrum of light transmitted through or reflected from the target part of the living body, it is generally necessary to perform measurement by positioning the target part of the living body at a predetermined position relative to a light projecting member and/or a light receiving element for receiving the transmitted or reflected light.

Hitherto, for biological information measurement, the use has been made of a clip-type probe for biological information measurement of a biological information measuring probe secured to the target part of the living body by the use of a double-adhesive tape (such as disclosed in, for example, the Japanese Laid-open Patent Publication No. 6-14906). During the biological information measurement using the clip-type biological information measuring probe, the target part of the living body is sandwiched by a spring mechanism between one clip member embedded with a light emitting element, and another clip member embedded with a light receiving element, such that light emitted from the light emitting element and transmitted through the target part of the living body is received by the light receiving element to accomplish biological information measurement. On the other hand, during the biological information measurement using the double-sided adhesive tape, a light emitting element and a light receiving element are secured in position by the use of the double-sided adhesive tape so as to confront with each other with the target part of the living body intervening therebetween so that, as is the case with the clip-type system, light emitted from the light emitting element and transmitted through the target part of the living body can be received by the light receiving element to accomplish the biological information measurement.

DISCLOSURE OF THE INVENTION

In, the biological information measurement in which the clip-type system or the double-sided adhesive tape is utilized, conditions for measurement at the target part tend to fluctuate when, once the biological information measuring probe has been removed from the target part of the living body, the biological information measuring probe is again fitted to the living body for re-measurement. Change in measurement data resulting from fluctuation of the measuring conditions are shown in FIGS. 11 and 12.

Measurement data shown in FIG. 11 were obtained as a result of the following measurement.

(1) Using an optical fiber, an energy spectrum (A) that provides the basis was measured by illuminating an initially selected target part of the palm of the hand of a subject, which is a part of the living body, with light, and receiving the light which has been reflected therefrom.

(2) An energy spectrum (B) was measured similarly by illuminating the target position after the target position, illuminated by the light, has been displaced 1 mm from an initially selected position without changing the angle of illumination (3) An energy spectrum (C) was measured similarly by illuminating the target position after the target position, illuminated by the light, has been displaced a further 1 mm, conveniently 2 mm from the initially selected position without changing the angle of illumination.

(4) An energy spectrum (D) was measured similarly by illuminating while resetting the position, illuminated by the light, to the initially selected position without changing the angle of, illumination when the subject having been administrated with an aqueous solution for sugar burden test, such as sold under "TRELAN 75" available from Shimizu Seiyaku Kabushiki Kaisha showed change of the subject's blood sugar reading by 15mg/dl.

(5) The energy spectra (A), (B), (C) and (D) were individually divided by the energy spectrum (A) measured at step (1) and the quotient was subsequently multiplied by 100 to give (E)={(A)/(A)}×100, (F)={(B)/(A)}×100, (G)={(C)/(A)}×100, (H)={(D)/(A)}×100.

(6) (E) was subtracted from (F) to give a curve $h_1$ shown in FIG. 11, (E) was subtracted from (G) to give a curve $h_2$ shown in FIG. 11, and (E) was subtracted from (H) to give a curve $h_3$.

On the other hand, in FIG. 12, using an optical fiber, an energy spectrum (A) that provides the basis was measured by illuminating an initially selected target part of the palm of the hand of a subject, which is a part of the living body, with light, and receiving the light which has been reflected therefrom, and thereafter, in steps (2) and (3) above, energy spectra were measured by changing the angle of illumination by 1, 2, 3 and 4 degrees, rather than changing the initially selected position of the target part to be measured being changed. Then, the energy spectrum was measured when the subject administrated with an aqueous solution for oral glucose tolerance test showed the subject's blood sugar reading of 15mg/dl, followed by calculation performed in manners similar to steps (5) and (6) to give respective curves $h_{11}$, $h_{12}$, $h_{13}$, $h_{14}$ and $h_3$.

Referring to FIGS. 11 and 12, comparing respective points of the curves at 1,667 nm (6,000 cm$^{-1}$) which is the absorption wavelength of glucose, while the energy spectrum fluctuated about 2.75% corresponding to change of the blood sugar value of 15 mg/dl exhibited during the oral glucose tolerance test, 1 mm displacement in position of the target part resulted in the energy spectrum having fluctuated about 4.88% and 1° displacement in angle resulted in the energy spectrum having fluctuated about 0.29%. Considering that measurement of glucose in the living body requires a resolution of 1 mg/dl, change of 0.18% converted must necessarily be measured. Accordingly, reproducibility of about 0.04 mm or smaller in position of the target part and about 0.62° or smaller in angle of illumination is required.

However, in the case of the method in which the clip-type probe for biological information measurement is used, it is difficult to reposition accurately the biological information measuring probe at the initially selected target part since individual living bodies have different shapes and/or sizes.

Also, in the case of the method in which the double-sided adhesive tape is used to secure the biological information measuring probe to the target part of a living body, it is difficult to secure accurately the biological information measuring probe to the initially selected target part. For these reasons, both of the clip-type system and the system of using the double-sided tape are ineffective to achieve the above described reproduction accuracy, resulting in varying measurement results and, therefore, they involve a problem in that no faithfully reproduced results can be obtained. Moreover, according to the method in which the clip-type biological information measuring system is used, when the concentration of a particular component of the target part which is a part of a living body is to be measured, there is the possibility that blood vessels may be pressed to such an extent as to adversely affect the blood flow, failing to provide stable measurement results.

An object of the present invention is to provide a method of positioning the living body effective to reposition the target part of the living body with high reproducibility.

Another object of the present invention is to provide a positioning device for biological information measurement effective to reposition the target part of the living body with high reproducibility without pressing any blood vessel of the living body.

A further object of the present invention is to provide a biological information measuring apparatus effective to give biological information measurements of high accuracy with minimized variation.

BEST MODE FOR CARRYING OUT THE INVENTION

Figure 1:
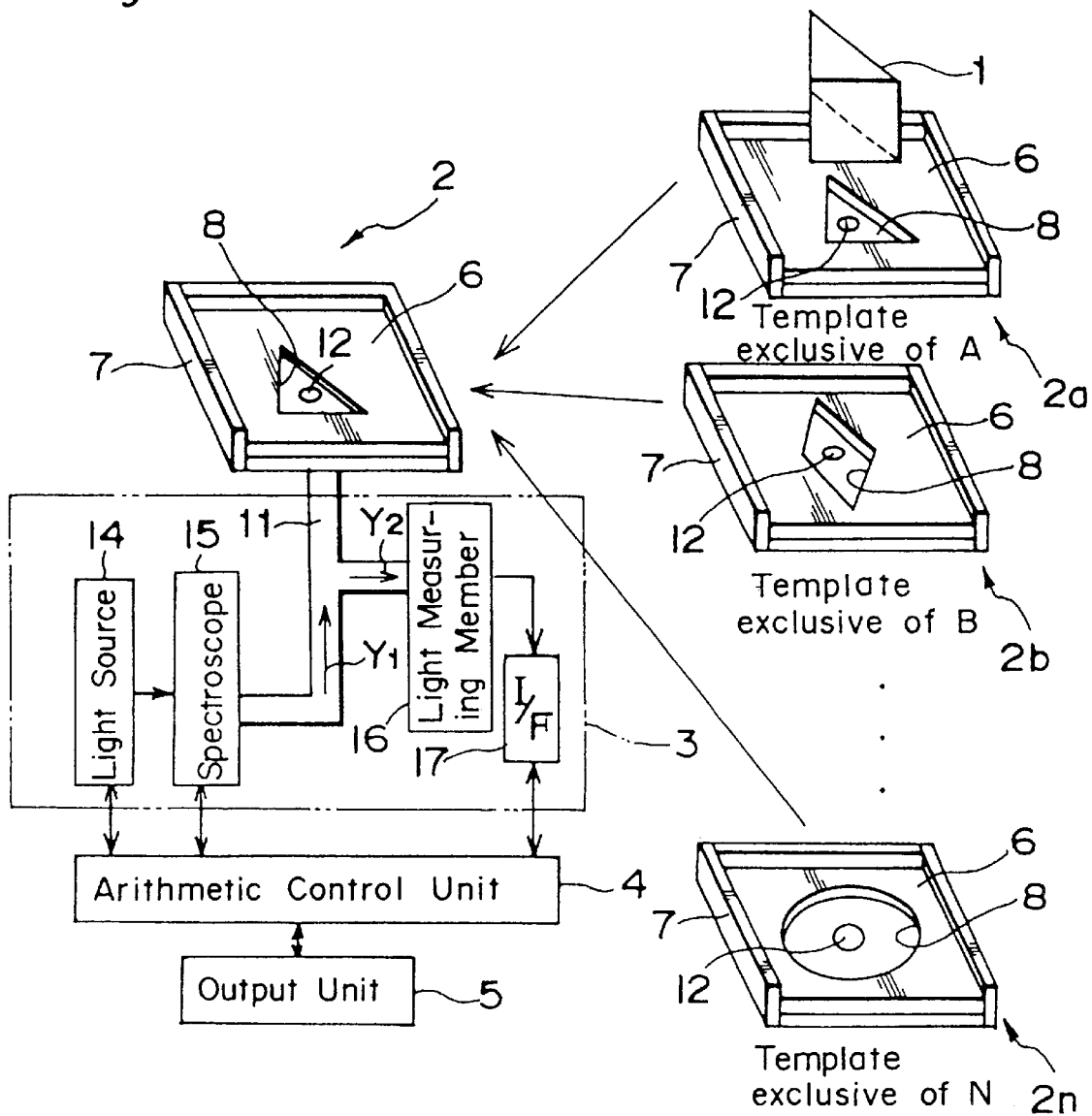
FIG. 1 is an explanatory diagram showing the structure of a biological information measuring apparatus and templates for the biological information measurement according to a first preferred embodiment of the present invention.

The present invention as defined in claim 1 is directed to a living body positioning method of positioning a target part of a living body during noninvasive measurement of the concentration of a particular component in the living body by the use of a transmitted or reflected spectrum that is obtained by illuminating the target part of the living body, which method is characterized by preparing a template for positioning the target part of the living body and positioning the target part of the living body relative to an optical system for measurement of a transmitted or reflected spectrum by the use of the template.

The present invention as defined in claim 2 is directed to a positioning device for biological information measurement for positioning a target part of a living body during noninvasive measurement of the concentration of a particular component in the living body by the use of a transmitted or reflected spectrum that is obtained by illuminating the target part of the living body, which method is characterized by the provision of a biological information measuring template means including a shape memory medium having a contact surface which, when the target part is pressed to the contact surface, undergoes change according to the shape of the target part, said shape memory medium being operable to store the shape, the target part of the living body being positioned at a store portion of the shape memory medium of the biological information measuring template means.

The present invention as defined in claim 3 is characterized in that, in the invention as defined in claim 2, the biological information measuring template means includes a stationary casing accommodating therein the shape memory medium and formed with a transmitting hole defined therein for passage therethrough of the light to be illuminated onto the target part of the living body.

The present invention as defined in claim 4 is characterized in that in the invention as defined in claim 2 or 3, the shape memory medium is a material such as a rubber material, a soft resinous material, a hard resinous material or a plasticizeable inorganic material.

The present invention as defined in claim 5 is characterized in that in the invention as defined .in claim 2, the shape memory medium comprises a plurality of movable rods axially displaceable when respective ends thereof are brought into contact with the target part of the living body.

The present invention as defined in claim 6 is characterized in that in the invention as defined in claim 5, the plural movable rods are juxtaposed with each other.

The present invention as defined in claim 7 is characterized in that in the invention as defined in claim 5, the plural movable rod are arranged radially.

The present invention as defined in claim 8 is characterized in that in the invention as defined in any one of claims 5 to 7, there is provided a displacement detecting sensor for detecting displacement of the plural movable rods, a storage device for storing the displacement detected, and a drive device for reproducing a position of the movable rods according to the stored displacement.

The present invention as defined in claim 9 is directed to a biological information measuring apparatus for measuring the concentration of a particular component in a living body by the use of a transmitted or reflected spectrum that is obtained by illuminating the target part of the living body, which apparatus is characterized in the provision of a biological information measuring template means including a shape memory medium having a contact surface which, when the target part is pressed to the contact surface, undergoes change according to the shape of the target part, said shape memory medium being operable to store the shape, said biological information measuring template means being operable to project light onto the target part positioned at a store portion of the shape memory medium and then to receive a transmitted or reflected light from the target part; an arithmetic processing means for arithmetically processing a spectrum of the transmitted or reflected light from the target part which has been received by the biological information measuring template means, to thereby calculate the concentration of the particular component in the living body; and an output means for outputting the calculated concentration of the particular component.

The target part of the living body is positioned relative to the measurement optical system by means of the template of the target part of the living body which have been prepared beforehand.

The shape memory medium has the contact surface which, when the target part is pressed to the contact surface, undergoes change according to the shape of the target part. The target part of the living body is arranged at the store portion of the shape memory medium which has changed according to the shape of the target part of the living body.

Also, the shape memory medium is supported and fixed within a stationary casing, and the light is projected onto the target part of the living body through a transmitting hole defined in the stationary casing.

Moreover, the shape memory medium is made of a material such as a rubber material, a soft resinous material, a hard resinous material or a plasticizeable inorganic material.

The plural movable rods of the shape memory medium are axially displaced when respective ends thereof are brought into contact with the target part of the living body.

Moreover, when the target part of the living body contacts the respective ends of the plural movable rods of the shape memory medium, the movable rods which are brought into contact with the target part of the living body are displaced in the same direction according to the shape of the target part of the living body.

In addition, when the target part of the living body contacts a radially center portion of the radially arranged plural rods of the shape memory medium, the movable rods which are brought into contact with the target part of the living body are displaced radially according to the shape of the target part of the living body.

The displacement detecting sensor detects the displacement of the plural movable rods, the memory device stores the detected displacement, and the drive device reproduces the position of the movable rods according to the displacement stored in the memory device.

Furthermore, the shape memory medium of the biological information measuring template means stores the shape of the contact portion thereof when as a result of the target part of the living body having been pressed against the contact surface the contact surface undergoes change in shape, the light being projected onto the target part which has been arranged at the store portion of the shape memory medium and the transmitted or reflected light being received from the target part, and the arithmetic processing means performs an arithmetic process on the spectrum of the transmitted or reflected light from the target part which has been received, to thereby calculate the concentration of the particular component in the living body, with the output means subsequently outputting the calculated concentration of the particular component.

Hereinafter, embodiments of the present invention will be described with reference to the accompanying drawings.

(Embodiment 1)

The structure of a biological information measuring apparatus according to one embodiment of the present invention is shown in FIG. 1. The biological information measuring apparatus shown in FIG. 1 includes a biological information measuring template 2 on which a target part 1 of a living body is placed, a measuring optical system 3 for projecting near-infrared light onto the target part 1 through the biological information measuring template 2 and for detecting the intensity of the light reflected therefrom, an arithmetic control unit 4 for arithmetically processing the intensity of the reflected light detected by the measuring optical system 3 to detect the concentration of a particular component contained in the target part 1 of the living body, and an output unit 5 for the arithmetic control unit 4.

The biological information measuring template 2 includes a shape memory medium 6 having a contact surface which deforms according to the shape of an object when the object is pressed against such template 2, and also having a shape memory function of retaining a condition thereof and to store the shape of the object, and a stationary casing 7 for supporting the shape memory medium 6. The shape memory medium having the above described shape memory function may be in from of a rubber material, a soft resinous material, a hard resinous material or a plasticizeable inorganic material. The rubber material referred to above includes latex rubber, silicone rubber, urethane rubber, polyisoprene rubber, butadiene rubber, butyl rubber, ethylene-propylene rubber and so on. The soft resinous material referred to above includes EVA resin, polyvinyl chloride and so on. The hard resinous material referred to above includes urethane resin, silicone resin, alkyd resin, amino resin, aryl resin, epoxy resin, polyamide, metacrylic resin, polyester resin, and the inorganic plasticizeable material includes plaster or the like.

The shape memory medium 6 is poured in a fluid state into the stationary casing 7. While the shape memory medium 6 poured into the stationary casing 7 is in a deformable condition, the target part 1 of the living body is pressed. In this way, a portion of the shape memory medium 6 where the target part 1 of the living body has contacted is formed with an indentation 8 corresponding to the shape thereof to thereby take an impression of the target part 1 of the living body. When while in this condition the shape memory medium 6 is solidified, a template 2a of the target part of a living body A, a template 2b of the target part of a living body B, . . . and a template 2n of the target part of a living body N can be obtained.

Figure 2:
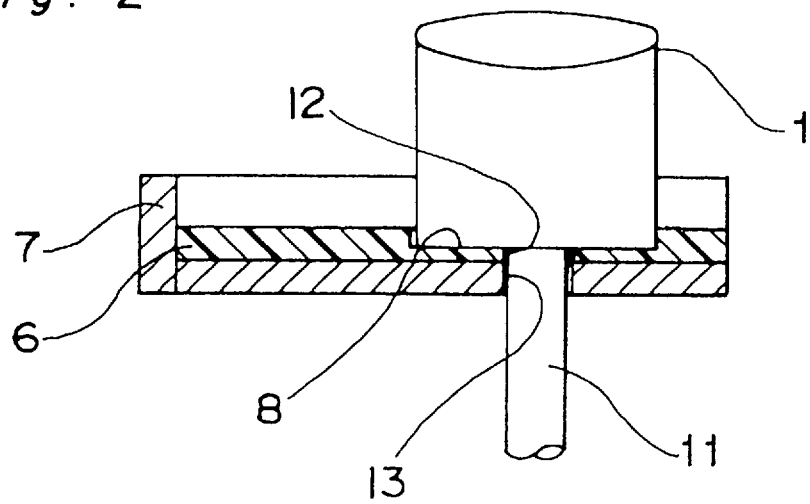
FIG. 2 is a sectional view showing the structure of the template for the biological information measurement shown in FIG. 1.
Figure 3:
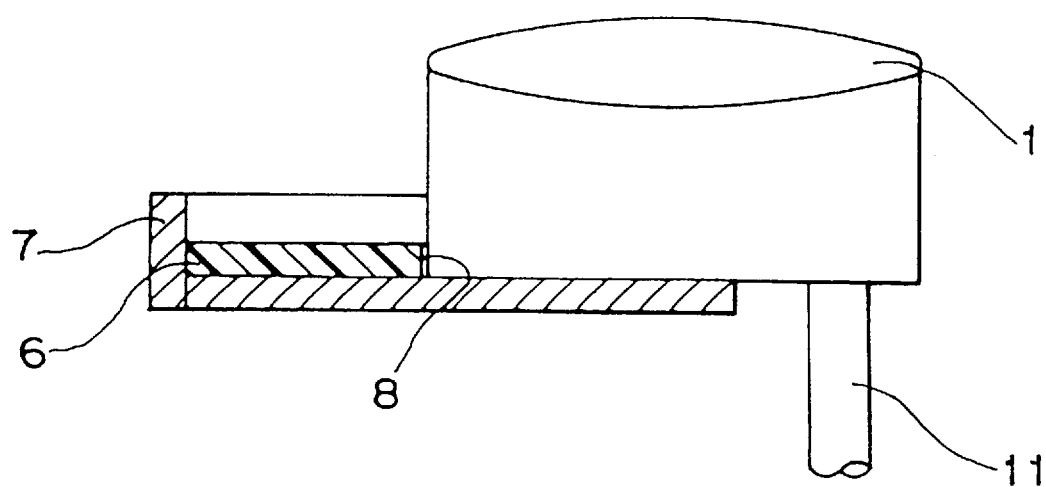
FIG. 3 is a sectional view showing the different structure of the template for the biological information measurement shown in FIG. 1.

As shown in FIG. 2, the shape memory medium 6 and the stationary casing 7 are formed from rear of the indentation 8 of the target part 1 of the living body with transmitting holes 12 and 13, respectively, through which an optical fiber 11 for projecting the near-infrared light onto the target part 1 of the living body and receiving the light reflected therefrom as will be described later is inserted. It is to be noted that as shown in FIG. 3, the target part 1 of the living body may be positioned by the shape memory medium 6 supported and fixed in position within the stationary casing 7 and the optical fiber 11 is selected outside the stationary casing 7 and then arranged so as to have a predetermined positional relation with the position of the stationary casing 7.

As shown in FIG. 1, the measuring optical system 3 includes a light source 14 for emitting light containing the near-infrared light, a spectroscope 15 for analyzing the light emitted from the light source 14, the optical fiber 11 for guiding the near-infrared light, analyzed by the spectroscope 15, towards the biological information measuring template 2 (See the arrow $Y_1$ in FIG. 1) and also for guiding the light, reflected from the target part 1 of the living body positioned by the shape memory medium 6 of the biological information measuring template 2, towards a light measuring member 16 (See the arrow $Y_2$ in FIG. 1), the light measuring member 16 for measuring the intensity of the reflected light from the target part 1 of the living body which has been transmitted through the optical fiber 11, and an interface circuit 17 for amplifying an output from the light measuring member 16 and converting it into a digital signal.

The arithmetic control unit 4 is comprised of a microcomputer and is operable to arithmetically calculate the signal intensity of the near-infrared light which has been inputted from the interface circuit 17 of the light measuring optical system 3 and which has been absorbed in proportion to the concentration of the particular component in the target part 1 of the living body, to thereby detect the concentration of the particular component of interest contained in the living body. The concentration of the particular component can be outputted to the output unit 5 which may be a cathode ray tube display and/or a printer. The light source 14, the spectroscope 15, the interface circuit 17 and the output unit 5 are controlled by a control signal supplied from the arithmetic control unit 4.

In the structure so far described, the shape memory medium 6 is injected into the stationary casing 7. While the shape memory medium 6 is in a deformable condition, the target part 1 of the living body A is pressed to the shape memory medium 6 to cause the latter to be indented according to the shape of the target part of the living body A to thereby take an impression exclusively of the target part 1 of the living body A, followed by solidification of the shape memory medium 6. Thereafter, from rear of the indentation 8 formed by the target part 1 of the living body A, the transmitting holes 12 and 13 are formed in the shape memory medium 6 and the stationary casing 7, respectively. Procedures similar to those carried out with respect to the living body A are carried out with respect to each of the living bodies B, ... and N to obtain the respective templates exclusive of the target part 1 thereof, and after solidification of the shape memory medium 6, the transmitting holes 12 and 13 are formed.

After the preparatory procedures as described above have been taken, in the case where the concentration of the particular component in the living body A is to be measured, the template 2a of the target part 1 of the living body A is employed, the optical fiber 11 is inserted into the transmitting holes 12 and 13 in the template 2a and fixed at a predetermined position, with the target part 1 of the living body A subsequently positioned within the indentation 8.

In this condition, the near-infrared light from the light source 14 of the light measuring optical system 3 is projected through the optical fiber 11 onto the target part 1 of the living body A. The light reflected therefrom is received by the light measuring member 16 of the light measuring optical system 3 through the optical fiber 11, and the signal intensity of the near-infrared light which has been absorbed at the target part 1 in proportion to the concentration of the particular component in the living body A is arithmetically calculated by the arithmetic control unit 4 to detect the concentration of the particular component of interest contained in the living body A which is subsequently displayed by means of the CRT display (not shown) of the output unit 5 and/or is printed out by the printer (not shown) of the output unit 5. By so doing, the indentation 8 formed in the shape memory medium 6 of the biological information measuring template 2a exclusive of A matches with the target part 1 of the living body A and, therefore, the target part 1 of the living body A can be positioned with good reproducibility. With respect to the template 2b exclusive of the living body B, ... and the template 2n exclusive of the living body N, by the same reason as that in the case of the template 2a exclusive of the living body A, the target part 1 thereof can be accurately positioned with good reproducibility. Accordingly, even through measurement is carried out repeatedly under the same measuring condition, the same part can be the subject of measurement at all times and, therefore, a measurement result of high reproducibility can be obtained.

(Embodiment 2)

Figure 4:
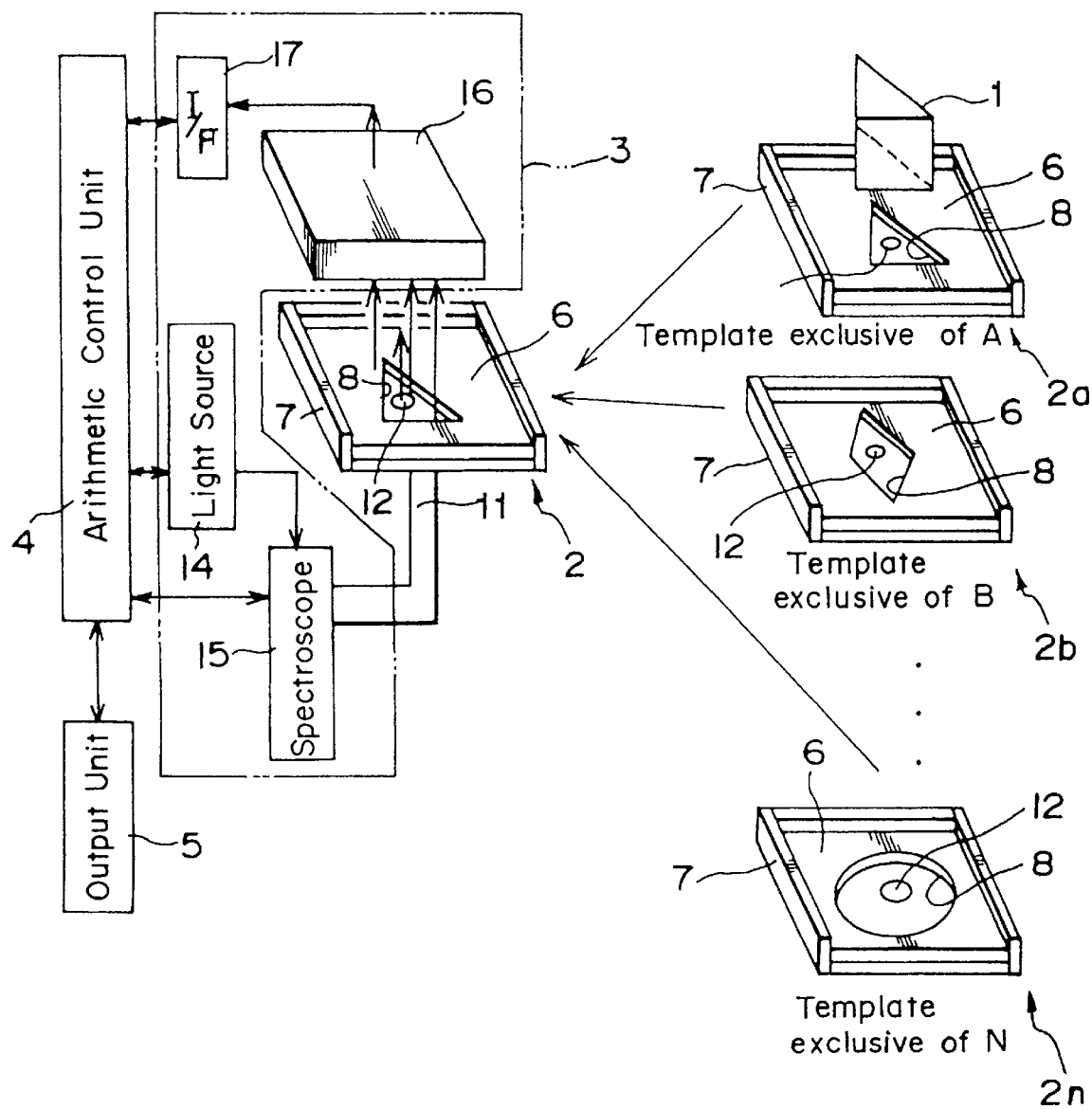
FIG. 4 is an explanatory diagram showing the structure of the biological information measuring apparatus and templates for the biological information measurement according to a second preferred embodiment of the present invention.

The biological information measuring apparatus according to another embodiment of the present invention is shown in FIG. 4. The biological information measuring apparatus shown in FIG. 4 is so designed that in the biological information measuring apparatus shown in and described with reference to FIG. 1, a light exit end of the optical fiber 11 for projecting the near-infrared light onto the target part 1 of the living body and the light measuring member 16 are positioned in opposition to and on respective sides of the target part 1 (See the template 2a exclusive of A shown in FIG. 4) positioned by the indentation 8 formed in the shape memory medium 6 of the biological information measuring template 2 wherefore the light intensity of the near-infrared light having transmitted through the target part 1 of the living body can be measured by the light measuring member 16. It is to be noted that in FIG. 4 component parts similar to those shown in FIG. 1 are designated by like reference numeral for the sake of brevity. Even with the biological information measuring apparatus shown in FIG. 4, the template 2a exclusive of the living body A, the template 2b exclusive of the living body B, ... and the template 2n exclusive of toe living body N are prepared in a manner similar to those with the biological information measuring apparatus of FIG. 1, and the concentration of the particular component of interest In each living body A to N can be detected at the target part 1 of the respective living body A to N.

(Embodiment 3)

Figure 5:
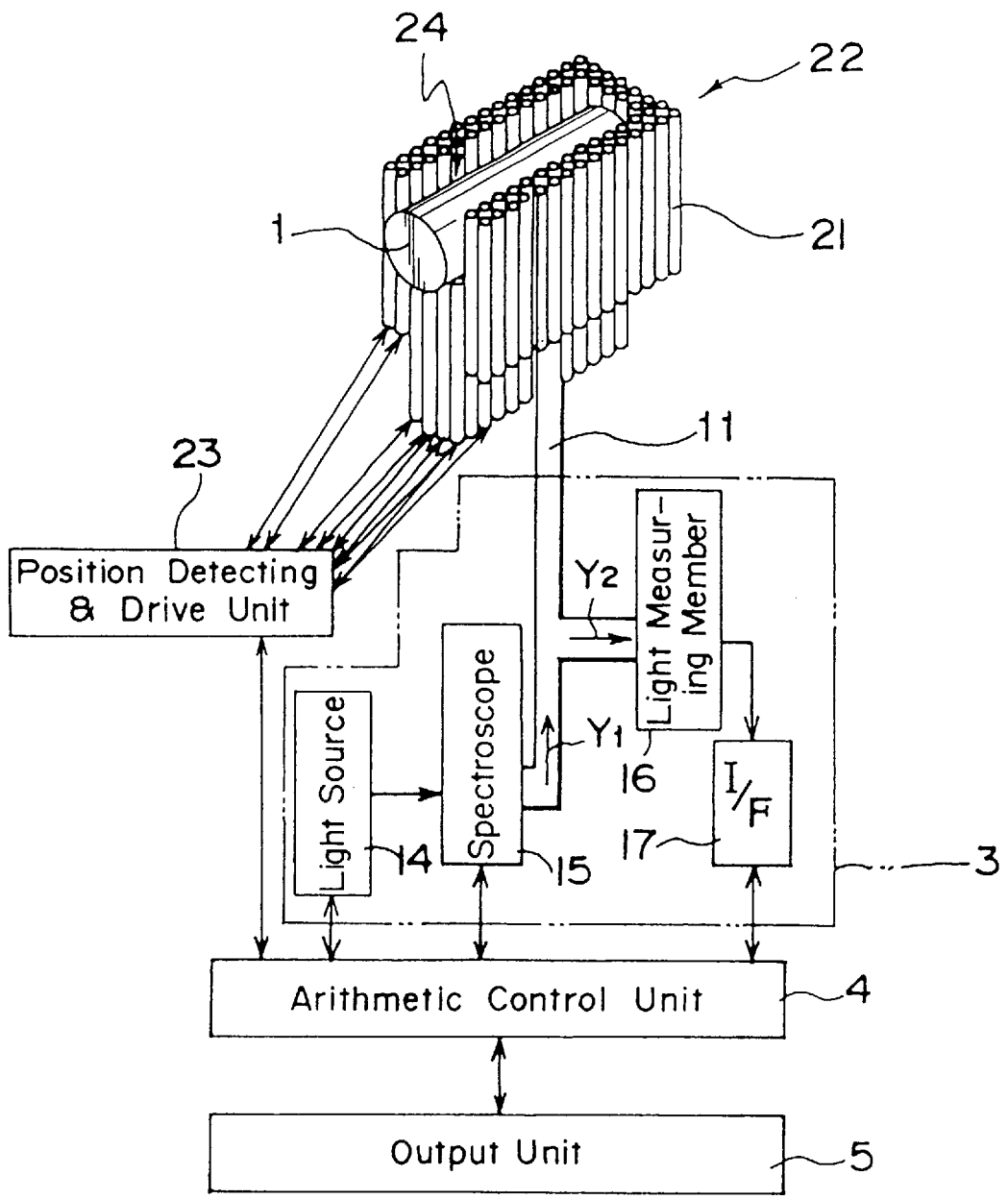
FIG. 5 is an explanatory diagram showing the structure of the biological information measuring apparatus according to a third preferred embodiment of the present invention.

The biological information measuring apparatus according to a further preferred embodiment of the present invention is shown in FIG. 5. In this biological information measuring apparatus shown in FIG. 5, in place of the biological information measuring template 2 provided with the shape memory medium 6 and the stationary casing 7, what is constituted by a plurality of movable rods 21 displaceable axially is used as a biological information measuring template 22. It is to be noted that in FIG. 5 component parts similar to those shown in FIG. 1 are designated by like reference numeral for the sake of brevity. In the biological information measuring template 22 shown in FIG. 5, the plural movable rods 21 are juxtaposed so as to extend parallel to each other and are arranged so as to render them as a whole to represent a parallelepiped form. In the biological information measuring template 22, the movable rods 21 have their respective front ends lying in the same plane and some of the movable rods 21 are removed for passage therethrough of the optical fiber 11.

Figure 6:
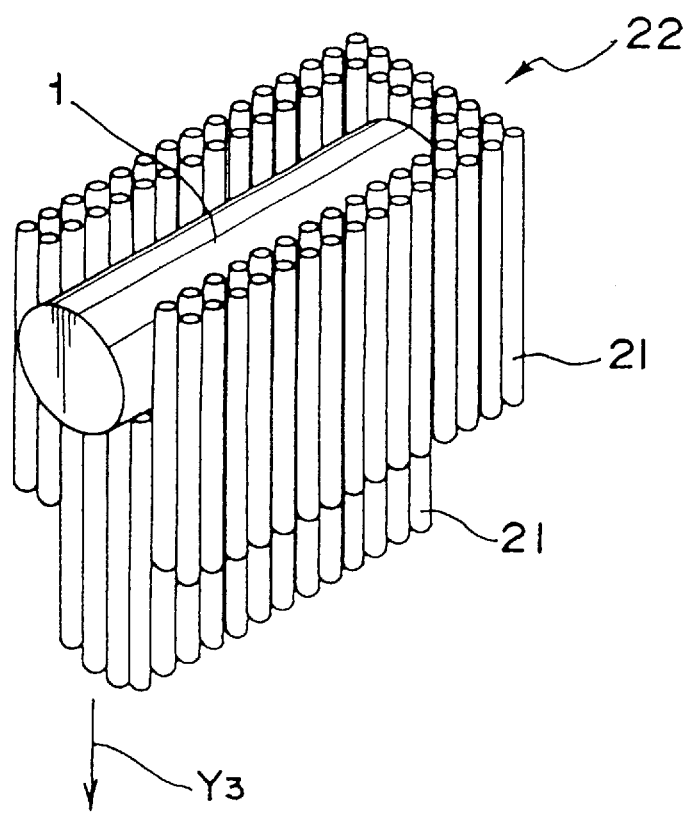
FIG. 6 is an explanatory diagram showing the template for the biological information measurement for use with the biological information measuring apparatus shown in FIG. 5.

In a mode for storage of the shape of the target part 1 of the living body, the target part 1 of the living body is placed on the plane defined by the front ends of the respective movable rods 21. By so doing, the movable rods 21 are displaced as shown by the arrow $Y_3$ in FIG. 6 according to the shape of the target part 1 of the living body. Respective displacements of the movable rods 21 are detected by a position detecting and driving unit 23, which is comprised of, for example, a potentiometer and an actuator, for detecting the position of and driving the movable rods 21 and are then stored in a memory (not shown) of the arithmetic control unit 4.

On the other hand, in a mode for reproducing the shape of the target part 1 of the living body, the position detecting and driving unit 23 shown in FIG. 5 drives the movable rods 21 in correspondence with the displacements of the respective movable rods 21 stored in the memory of the arithmetic control unit 4, to thereby reproduce the shape of the target part 1 stored during the storage mode. By arranging and positioning the target part 1 of the living body at the reproduced portion 24 of the shape, the concentration of the particular component of interest can be detected at the target part 1 of the living body in a manner similar to that with the biological information measuring apparatus shown in FIG. 1.

In this embodiment, since the shape of the target part of the living body is stored in the memory of the arithmetic control unit 4, the use of the single biological information measuring template 22 for different target parts of different living bodies is sufficient and, also, a process of storing the target part 1 of the living body can be simplified.

(Embodiment 4)

Figure 7:
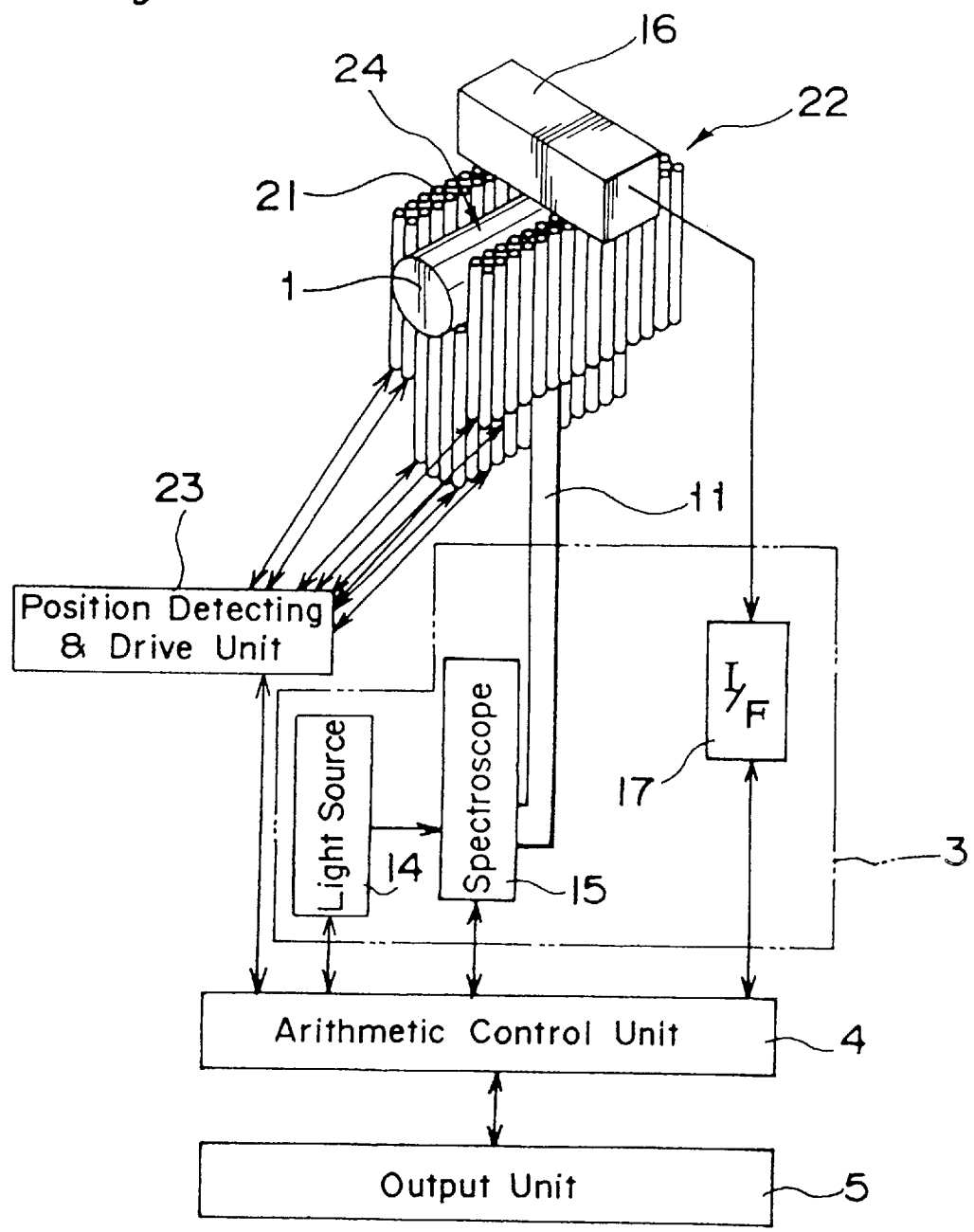
FIG. 7 is an explanatory diagram showing the structure of the biological information measuring apparatus according to a fourth preferred embodiment of the present invention.

The biological information measuring apparatus according to a still further preferred embodiment of the present invention is shown in FIG. 7. The biological information measuring apparatus shown in FIG. 7 is so designed that in the biological information measuring apparatus shown in and described with reference to FIG. 5, the light exit end of the optical fiber 11 for projecting the near-infrared light onto the target part 1 of the living body and the light measuring member 16 are positioned in opposition to and on respective sides of the target part 1 of the living body positioned by the reproduced portion 24 of the shape of the target part 1 of the living body formed in the biological information measuring template 22, wherefore the light intensity of the near-infrared light having transmitted through the target part 1 of the living body can be measured by the light measuring member 16. It is to be noted that in FIG. 7 component parts similar to those shown in FIG. 5 are designated by like reference numeral for the sake of brevity. Even with the biological information measuring apparatus shown in FIG. 7, as is the case with the biological information measuring apparatus shown in FIG. 5, by allowing the shape of the target part 1 of the living body to be stored in the memory of the arithmetic control unit 4, the use of the single biological information measuring template 22 for the different target part 1 of the different living bodies is effective to allow the concentration of the particular component of interest to be detected at the target part 1 of the living body.

(Embodiment 5)

Figure 8:
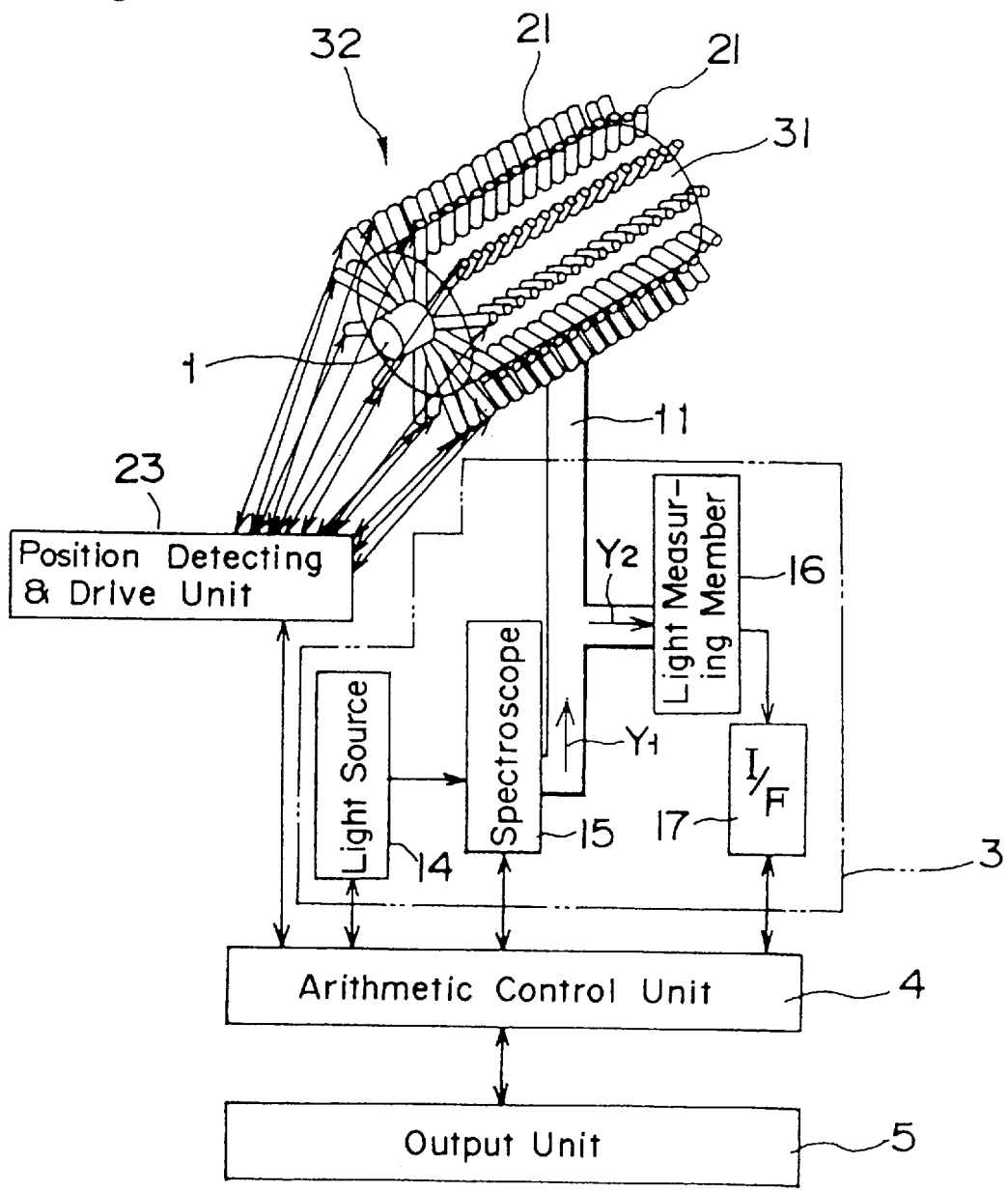
FIG. 8 is an explanatory diagram showing the structure of the biological information measuring apparatus according to a fifth preferred embodiment of the present invention.

The biological information measuring apparatus according to a still further preferred embodiment of the present invention is shown in FIG. 8. In the biological information measuring apparatus shown in FIG. 8, in place of the biological information measuring template 22 in which the plural movable rods 21 are arranged so as to represent the parallelepiped form as described with reference to FIG. 5, a biological information measuring template 32 is employed of a type in which the plural movable rods 21 are supported by a cylindrical support member 31 so as to extend radially. It is to be noted that in FIG. 8 component parts similar to those shown in FIG. 5 are designated by like reference numeral for the sake of brevity. In the biological information measuring template 32, the movable rods 21 have their respective front ends oriented towards a longitudinal center portion of the cylindrical support member 31 and some of the movable rods 21 are removed for passage therethrough of the optical fiber 11.

Figure 9:
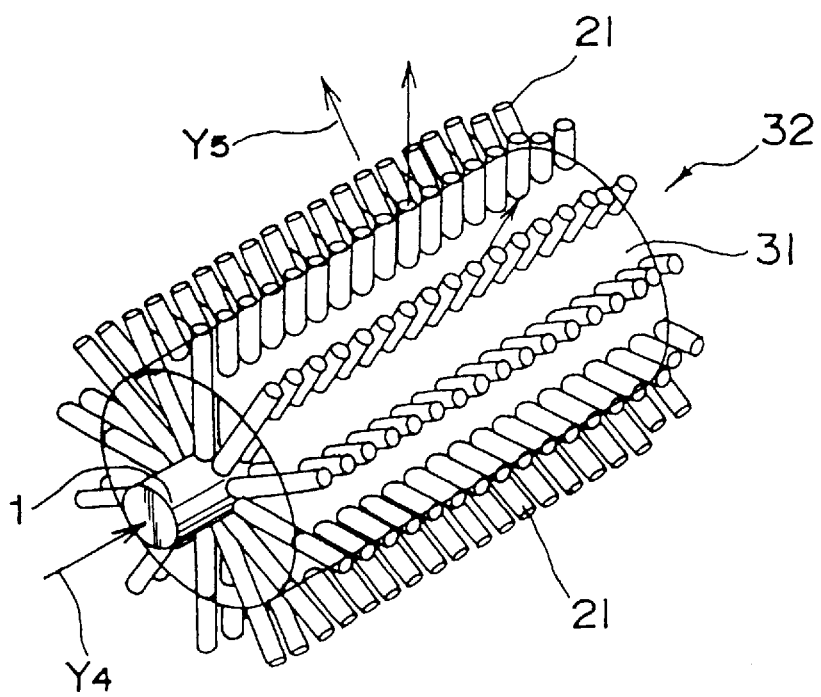
FIG. 9 is an explanatory diagram showing the template for the biological information measurement for use with the biological information measuring apparatus shown in FIG. 8.

In a mode for storage of the shape of the target part of the living body, the target part 1 of the living body is inserted into the longitudinal center portion of the cylindrical support member as shown by the arrow $Y_4$ in FIG. 9. By so doing, the movable rods 21 are displaced as shown by the arrow $Y_5$ in FIG. 9 according to the shape PPF the target part 1 of the living body. Respective displacements of the movable rods 21 are stored in the memory (not shown) of the arithmetic control unit 4 in a manner similar to that in the embodiment of FIG. 5.

On the other hand, in a mode for reproducing the shape of the target part of the living body, in a manner similar to that in the embodiment of FIG. 5, the shape of the target part 1 of the living body stored during the storage mode is reproduced by the front ends of the plural movable rods 21 in a manner similar to that in the embodiment of FIG. 5. By inserting and positioning the target part 1 of the living body at the reproduced portion of the shape, the concentration of the particular component of interest can be detected at the target part 1 of the living body in a manner similar to that with the biological information measuring apparatus shown in FIG. 1.

In this embodiment, the use of the single biological information measuring template 32 for different target parts of different living bodies is sufficient and, also, not only can a process of storing the target part 1 of the living body can be simplified, but the target part 1 of the living body can be positioned from all directions of 360°.

(Embodiment 6)

Figure 10:
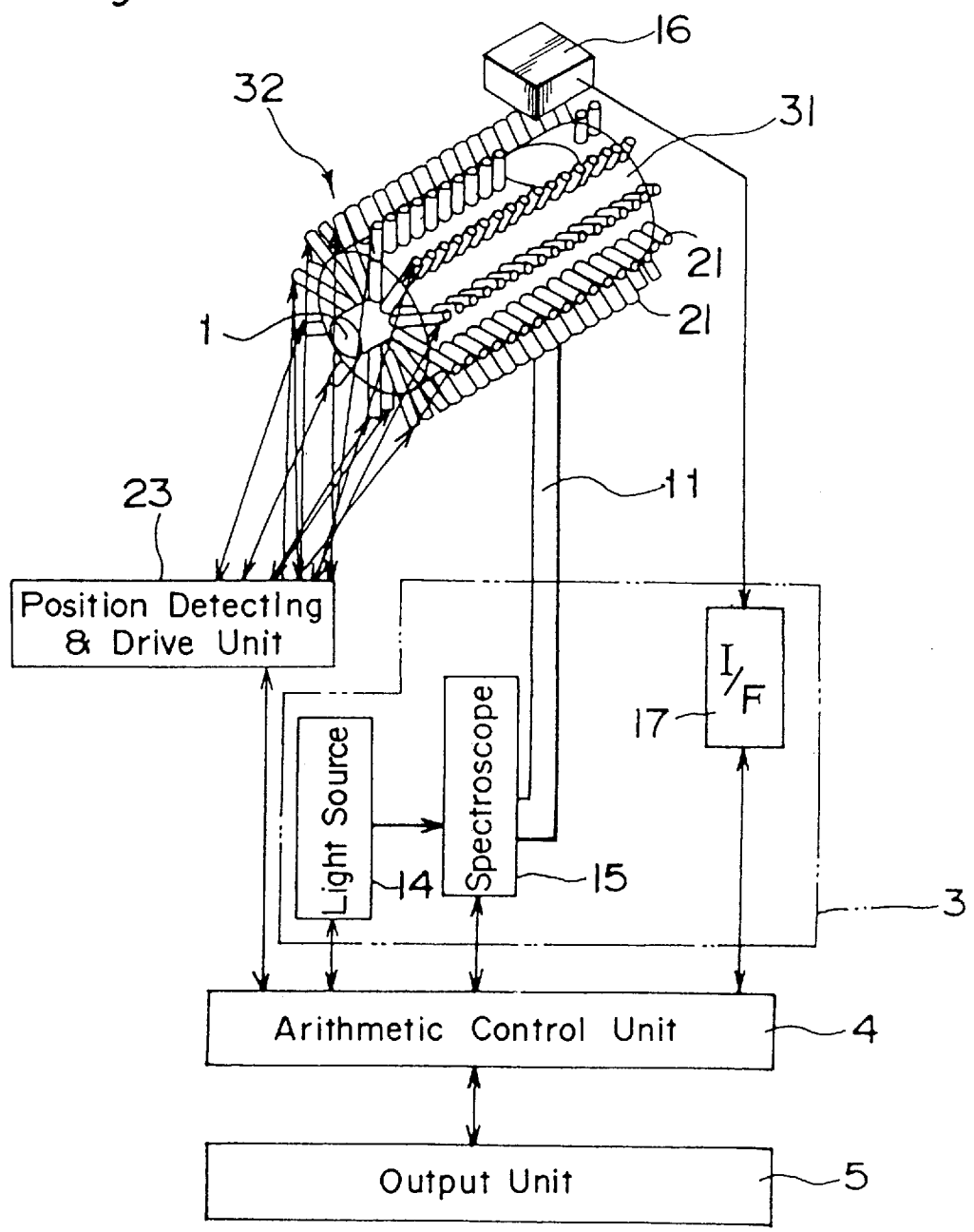
FIG. 10 is an explanatory diagram showing the structure of the biological information measuring apparatus according to a sixth preferred embodiment of the present invention.
Figure 11:
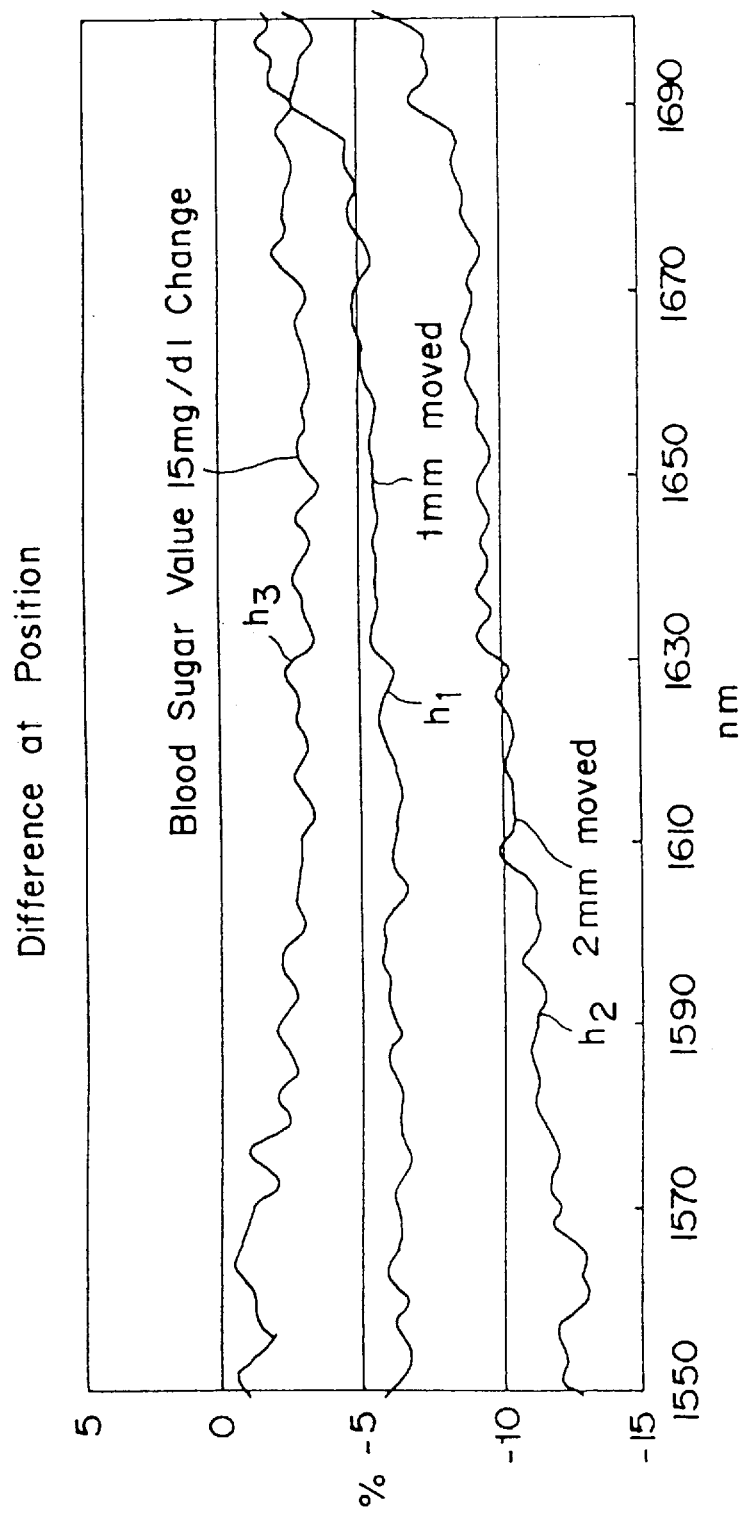
FIG. 11 is a measurement date showing change in spectrum with change in position of the target part when the angle of projection of light is fixed.
Figure 12:
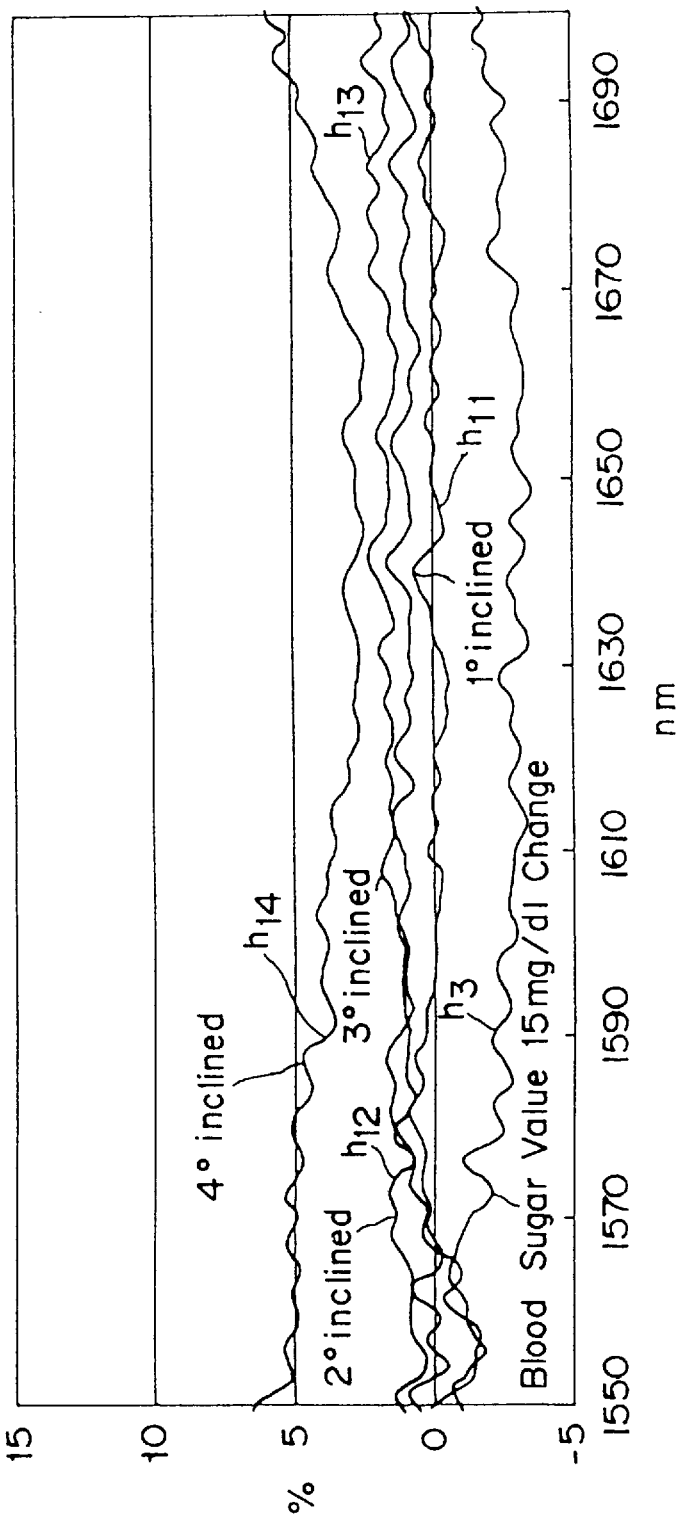
FIG. 12 is a measurement date showing change in spectrum with change in angle of projection of light without the position of the target part being changed.

The biological information measuring apparatus according to a yet further preferred embodiment of the present invention is shown in FIG. 10. The biological information measuring apparatus shown in FIG. 10 is so designed that in the biological information measuring apparatus shown in and described with reference to FIG. 8, the light exit end of the optical fiber 11 for projecting the near-infrared light onto the target part 1 of the living body and the light measuring member 16 are positioned in opposition to and on respective sides of the target part 1 of the living body positioned by the biological information measuring template 32, wherefore the light intensity of the near-infrared light having transmitted through the target part 1 of the living body can be measured by the light measuring member 16. It is to be noted that in FIG. 10 component parts similar to those shown in FIG. 8 are designated by like reference numeral for the sake of brevity. Even with the biological information measuring apparatus shown in FIG. 10, as is the case with the biological information measuring apparatus shown in FIG. 8, by allowing the shape of the target part 1 of the living body to be stored in the memory of the arithmetic control unit 4, the use of the single biological information measuring template 32 for the different target part 1 of the different living bodies is effective to allow the concentration of the particular component of interest to be detected at the target part 1 of the living body.

Industrial Applicability

According to the present invention, since the target part of the living body is positioned relative to the measurement optical system by means of the template of the target part of the living body which have been prepared before-hand, the target part of the living body can be arranged at the same position with good reproducibility.

Also, according to the present invention, since the shape memory medium has the contact surface which, when the target part is pressed to the contact surface, undergoes change according to the shape of the target part, by arranging the target part of the living body at the store portion of the shape memory medium which has changed according to the shape of the target part of the living body, not only can the target part of the living body be accurately positioned with high reproducibility, but also no blood vessel will be pressed.

Further, according to the present invention, since the light is projected onto the target part of the living body through the transmitting hole in the stationary casing, the target part of each living body can be positioned with high reproducibility to accomplish the biological information measurement.

Moreover, according to the present invention, by constructing the shape memory medium with a material such as a rubber material, a soft resinous material, a hard resinous material or a plasticizeable inorganic material, the target part of the living body can be reproduced with high reproducibility with a simplified structure using the inexpensive material.

Furthermore, according to the present invention, since the plural movable rods of the shape memory medium are axially displaced when respective ends thereof are brought into contact with the target part of the living body to thereby store the shape of the target part of the living body, neither process nor time required in solidifying the shape memory medium at the time of storing the shape of the target part of the living body is needed and storage of the shape of the target part of the living body can be accomplished simply.

Yet, according to the present invention, since when the target part of the living body contacts the respective ends of the plural movable rods of the shape memory medium, the movable rods which are brought into contact with the target part of the living body are displaced in the same direction according to the shape of the target part of the living body, mere placement of the target part of the living body on the shape memory medium is effective to simply store the shape of the target part of the living body.

In addition, according to the present invention, since when the target part of the living body contacts a radially center portion of the radially arranged plural rods of the shape memory medium, the movable rods which are brought into contact with the target part of the living body are displaced radially according to the shape of the target part of the living body, the shape of the target part of the living body can be stored merely by inserting the target part of the living body into the shape memory medium and the target part of the living body can be positioned from all directions of 360°, resulting in considerable increase of the reproducibility.

Again, according to the present invention, since the displacement detecting sensor detects the displacement of the plural movable rods, the memory device stores the detected displacement and the drive device reproduces the position of the movable rods according to the displacement stored in the memory device, the use of the single shape memory medium is effective to store the shape of the target part of each of the plural living bodies.

Moreover, according to the present invention, since by arranging the target part of the living body at the stored portion of the memory medium the target part of the living body can be positioned with high reproducibility without pressing the blood vessel in the living body, the concentration of the particular component in the living body can be measured with high reproducibility by causing the arithmetic processing means to perform the arithmetic processing of the spectrum of the transmitted or reflected light from the target part.

What is claimed is:

1. A living body positioning method of positioning a target part of a living body during noninvasive measurement of the concentration of a particular component in the living body by the use of a transmitted or reflected spectrum that is obtained by illuminating the target part of the living body, which method comprises:

prior to a first cycle of measurement of the concentration, preparing a template for positioning the target part of the living body having a means for reproducing the shape of the target part of the living body;

performing the first cycle of measurement of the concentration by allowing the reproducing means in the template to receive the target part and by positioning the target part of the living body, which has been received in the reproducing means in the template, relative to an optical system so as to align at least a portion of the target part with an optical sensor, that is fitted to the template, for measurement of a transmitted or reflected spectrum;

removing the template from the target part after the first cycle of measurement of the concentration; and at the time a subsequent cycle of measurement of the concentration is to be performed, positioning the same target part of the same living body within the same reproducing means in the same template with that portion of the target part aligned substantially exactly with the optical sensor, thereby enabling substantially the same target part of the living body to be remeasured.

2. A positioning device for biological information measurement for positioning a target part of a living body during noninvasive measurement of the concentration of a particular component in the living body by the use of a biological information measuring apparatus which comprises an optical light source for projecting light onto the target part and an optical sensor for receiving a transmitted or reflected light from the target part, and means for processing a spectrum of the transmitted or reflected light from the target part of the living body to thereby calculate the concentration of the particular component in the living body, said target part having a predetermined shape, which device comprises:

a template having a means for reproducing the shape of the target part of the living body, wherein said template comprises:

a shape memory medium, comprising:

a contact surface which, when the target part is pressed to the contact surface, undergoes change according to the shape of the target part to define therein the reproducing means, complemental in shape to the shape of the target part, said shape memory medium being operable to store the shape of the target part, the target part of the living body being positioned within and restrained by the reproducing means, said reproducing means substantially permanently storing the shape of the target part such that whenever the target part is placed in the reproducing means in the template, the same target part can be positioned in the same reproducing means in the same template with a portion of the target part substantially exactly aligned with the optical sensor thereby enabling substantially the same target part of the living body to be remeasured.

3. The positioning device for biological information measurement as claimed in claim 2, wherein said means for measuring biological information includes a stationary casing accommodating therein the shape memory medium and formed with a transmitting hole defined therein for passage therethrough of the light to be projected onto the target part of the living body.

4. The positioning device for biological information measurement as claimed in claim 2 or 3, wherein the shape memory medium is a material selected from the group consisting of a rubber material, a soft resinous material, a hard resinous material and a plasticizeable inorganic material.

5. A positioning device for biological information measurement for positioning a target part of a living body during noninvasive measurement of the concentration of a particular component in the living body by the use of a biological information measuring apparatus which comprises an optical light source for projecting light onto the target part and an optical sensor for receiving a transmitted or reflected light from the target part and means for processing a spectrum of the transmitted or reflected light from the target part of the living body to thereby calculate the concentration of the particular component in the living body, which device comprises:

a template for positioning the target part of the living body, wherein said template comprises:

a shape memory medium, comprising:

(a) a plurality of movable rods axially displaceable when respective ends thereof are brought into contact with the target part of the living body, to thereby store the shape of the target part of the living body being positioned at a store portion of the shape memory medium of the means for measuring biological information; and (b) means for reproducing the shape of the target part of the living body, thereby enabling substantially the same target part of the living body to be remeasured, said reproducing means comprising a displacement detecting sensor for detecting displacement of the plural movable rods; a storage device for storing the displacement detected; and a drive device for reproducing a position of the movable rods according to the stored displacement.

6. A living body positioning method of positioning a target part of a living body during noninvasive measurement of the concentration of a particular component in the living body by the use of a transmitted or reflected spectrum that is obtained by illuminating the target part of the living body, which method comprises:

prior to a first cycle of measurement of the concentration, preparing a template for positioning the target part of the living body having a memory shape medium for reproducing the shape of the target part of the living body;

performing the first cycle of measurement of the concentration by allowing the memory shape medium in the template to receive the target part and by positioning the target part of the living body, which has been received in the memory shape medium in the template, relative to an optical system so as to align at least a portion of the target part with an optical sensor, that is fitted to the template, for measurement of a transmitted or reflected spectrum;

removing the template from the target part after the first cycle of measurement of the concentration; and at the time a subsequent cycle of measurement of the concentration is to be performed, positioning the same target part of the same living body within the same memory shape medium in the same template with that portion of the target part aligned substantially exactly with the optical sensor, thereby enabling substantially the same target part of the living body to be remeasured.

7. The positioning device for biological information measurement as claimed in claim 5, wherein the plural movable rods are juxtaposed with respect to each other.

8. The positioning device for biological information measurement as claimed in claim 5, wherein the plural movable rods are arranged radially.

* * * * *